(12) United States Patent
Merat

(10) Patent No.: US 10,111,825 B2
(45) Date of Patent: *Oct. 30, 2018

(54) OIL-IN-WATER EMULSIONS ENRICHED WITH SALT WHICH ARE HIGHLY VISCOUS AND STABLE OVER TIME

(71) Applicant: SOCIETE D'EXPLOITATION DE PRODUITS POUR LES INDUSTRIES CHIMIQUES SEPPIC, Paris (FR)

(72) Inventor: Emmanuelle Merat, Lautrec (FR)

(73) Assignee: SOCIETE D'EXPLOITATION DE PRODUITS POUR LES INDUSTRIES CHIMIQUES SEPPIC, Paris (FR)

(*) Notice: Subject to any disclaimer, the term of this patent is extended or adjusted under 35 U.S.C. 154(b) by 513 days.

This patent is subject to a terminal disclaimer.

(21) Appl. No.: 14/362,639

(22) PCT Filed: Dec. 5, 2012

(86) PCT No.: PCT/FR2012/052802
§ 371 (c)(1),
(2) Date: Jun. 4, 2014

(87) PCT Pub. No.: WO2013/083912
PCT Pub. Date: Jun. 13, 2013

(65) Prior Publication Data
US 2014/0335039 A1  Nov. 13, 2014

(30) Foreign Application Priority Data
Dec. 8, 2011  (FR) .................... 11 61303

(51) Int. Cl.
| | |
|---|---|
| *A61K 8/81* | (2006.01) |
| *A61Q 5/00* | (2006.01) |
| *A61Q 19/10* | (2006.01) |
| *A61K 8/92* | (2006.01) |
| *A61K 8/06* | (2006.01) |
| *A61K 8/37* | (2006.01) |
| *A61K 8/20* | (2006.01) |
| *A61Q 19/00* | (2006.01) |
| *A61Q 5/02* | (2006.01) |
| *A61K 8/73* | (2006.01) |
| *A61Q 17/04* | (2006.01) |

(52) U.S. Cl.
CPC .......... *A61K 8/8158* (2013.01); *A61K 8/062* (2013.01); *A61K 8/20* (2013.01); *A61K 8/37* (2013.01); *A61K 8/737* (2013.01); *A61K 8/922* (2013.01); *A61Q 5/00* (2013.01); *A61Q 5/02* (2013.01); *A61Q 19/00* (2013.01); *A61Q 19/10* (2013.01); *A61K 2800/10* (2013.01); *A61K 2800/30* (2013.01); *A61K 2800/48* (2013.01); *A61K 2800/5424* (2013.01); *A61K 2800/72* (2013.01); *A61Q 17/04* (2013.01)

(58) Field of Classification Search
None
See application file for complete search history.

(56) References Cited

U.S. PATENT DOCUMENTS

| | | | |
|---|---|---|---|
| 2,798,053 A | 7/1957 | Brown | |
| 5,373,044 A | 12/1994 | Adams et al. | |
| 6,437,068 B2 | 8/2002 | Loffler et al. | |
| 6,645,476 B1 | 11/2003 | Morschhauser et al. | |
| 2006/0182824 A1* | 8/2006 | Lucas et al. | 424/757 |
| 2011/0274629 A1 | 11/2011 | Li et al. | |
| 2012/0172457 A1 | 7/2012 | Braun et al. | |

FOREIGN PATENT DOCUMENTS

| | | |
|---|---|---|
| EP | 0152095 A1 | 8/1985 |
| EP | 0301532 A2 | 2/1989 |
| EP | 0816403 A2 | 1/1998 |
| EP | 1069142 A1 | 1/2001 |
| EP | 1116733 A1 | 7/2001 |

(Continued)

OTHER PUBLICATIONS

Bernard et al., "A new polymer with a maximum resistance to electrolytes", SOFW-Journal, 2010, vol. 136, No. 12, pp. 55-58, XP055024800.

(Continued)

*Primary Examiner* — Nicole P Babson
(74) *Attorney, Agent, or Firm* — Young & Thompson

(57) ABSTRACT

Disclosed is a composition in the form of an oil-in-water emulsion, including: 5-55 wt % of an oil phase; 0.025-3.75 wt % of at least one cross-linked anionic polyelectrolyte resulting from the polymerization of partially or completely salified 2-methyl 2-[(1-oxo 2-propenyl) amino] 1-propanesulfonic acid, with at least one neutral monomer selected from acrylamide, (2-hydroxy ethyl) acrylate, and N,N-dialkyl arylamides. Each alkyl group includes 1-4 carbon atoms, and at least one monomer, where R is an alkyl radical including 8-20 carbon atoms and n is a number no smaller than one and no larger than twenty, in the presence of a cross-linking agent; 0.025-3.75 wt % of a galactomannan having a degree of substitution of approximately 1/3; 37.5-94.95 wt % of a cosmetically acceptable aqueous phase, the aqueous phase including 1-25 wt % of a salt, the weight ratio between the galactomannan and the cross-linked anionic polyelectrolyte being 1:3 to 3:1.

19 Claims, No Drawings

(56) References Cited

FOREIGN PATENT DOCUMENTS

| | | |
|---|---|---|
| FR | 2466273 A1 | 4/1981 |
| FR | 2910899 A1 | 7/2008 |
| FR | 2940111 A1 | 6/2010 |
| WO | 2011030044 A1 | 3/2011 |

OTHER PUBLICATIONS

Bernard, P., "Seppic's polymer with a maximum resistance to electrolytes", Internet Citation, 2010, pp. 1-22, XP002674160, http://lica.com.tw/english/licadata/seppic/SepiMAX%20ZEN.
International Search Report, dated Apr. 29, 2014, from corresponding PCT application.

* cited by examiner

OIL-IN-WATER EMULSIONS ENRICHED WITH SALT WHICH ARE HIGHLY VISCOUS AND STABLE OVER TIME

The invention relates to novel oil-in-water emulsions, as well as use thereof in cosmetics and pharmaceutics.

Cosmetic compositions presented in the form of oil-in-water emulsions marketed by the cosmetics industry and by the pharmaceutical industry very frequently comprise synthetic thickening polymers for increasing the viscosity of said oil-in-water emulsions which may be presented in the form of creams, lotions and which are applied directly to the skin.

These synthetic thickening polymers make it possible to thicken the aqueous phases present in said oil-in-water emulsions, thus obtaining either the desired consistency or a stabilisation effect of said emulsion.

The synthetic thickening polymers currently used in these fields are presented in two physical forms, powder form and liquid form for which the polymer is prepared by inverse emulsion radical polymerisation using surfactants, and commonly referred to as inverse latex.

Among the best known synthetic thickening polymers presented in powder form, powder form, mention can be made of polymers based on acrylic acid or copolymers based on acrylic acid and the esters thereof. Mention may be made for example of the polymers marketed under the brand name CARBOPOL™ and PEMULEN™. They are described in particular in the American patents U.S. Pat. No. 5,373,044 and U.S. Pat. No. 2,798,053 and in European patent EP 0 301 532.

In cosmetics, homopolymers or copolymers based on 2-acrylamido-2-methylpropane sulfonic acid and/or salts thereof are also used, again in powder form. These thickening polymers are marketed under the brand name Aristoflex™ and described in particular in the European patents EP 816 403, EP 1 116 733 and EP 1 069 142. These synthetic thickeners in powder form are obtained by precipitation polymerisation; the monomer(s) is (or are) placed in solution in an organic solvent such as benzene, ethyl acetate, cyclohexane, tertio-butanol; this method therefore requires numerous successive steps for purifying the end product, to remove any trace of residual solvent.

The cosmetics and pharmaceutical industries also very widely use thickeners presented in the form of inverse latexes and in particular those marketed by the applicant. Mention may be made for example of the thickeners Sepigel™ 305, Simulgel™ 600, Simulgel™ EG, Simulgel™ EPG, Simulgel™ NS, Simulgel™ A, Sepiplus™ 400, Sepiplus™ 250 and Sepiplus™ 265. These thickeners are obtained by inverse emulsion radical polymerisation. They have the advantage of being easier to handle, in particular at ambient temperature, and disperse very quickly in water. Furthermore, these products develop remarkably high thickening performances; these performances are probably the consequence of the method used for the preparation thereof, a dispersed phase radical polymerisation reaction, which results in polymers with very high molecular weights.

Nevertheless, these synthetic thickeners presented in the form of inverse latex contain an oil, and one or a plurality of surfactants which may sometimes induce skin intolerance reactions on particularly sensitive subjects; in addition this presence of oil makes them unusable for the preparation of clear aqueous gels.

The applicant has therefore developed synthetic thickeners having thickening performances equivalent or superior to inverse latexes, but better tolerated by the skin, in particular due to the absence of any oil phase that may lead to clearer aqueous gels. These products are presented in the form of powder but have dissolution times, and therefore ease of use, comparable to those of products in the form of liquids. These compounds, described in the European patent application published under the number EP 1 496 081, are obtained by the conventional polymerisation techniques, such as dispersed phase radical polymerisation, inverse suspension radical polymerisation, inverse emulsion or inverse microemulsion radical polymerisation. The synthetic thickening systems obtained are then extracted and purified by various techniques such as precipitation in a separate solvent, precipitation in a separate solvent optionally followed by washing, drying by atomisation or by azeotropic dehydration, optionally followed by washing by a carefully chosen solvent. These synthetic thickeners therefore combine some of the advantages of the synthetic thickeners in the form of conventional powders (absence of oil, obtaining of clearer aqueous gels) and the advantages of synthetic thickeners presented in the form of inverse latexes (high dissolution rate, remarkable thickening capacity and stabilising properties). However, for some uses, customers using such synthetic thickening systems wish to be able to manufacture gels that are even clearer than those obtained at the present time, or even transparent gels. In addition, the gels obtained with these synthetic thickeners do not have satisfactory stability when the composition is enriched with electrolytes, as is often the case with compositions comprising sun filters and/or coloured pigments and/or plant extracts enriched with electrolytes.

The applicant has also developed synthetic thickening systems such as those described in the French patent application published under the number 2 910 899, which discloses a linear, branched or cross-linked terpolymer of at least one monomer having a free, partially salified or completely salified strong acid function, with at least one neutral monomer, and at least one monomer of formula (A):

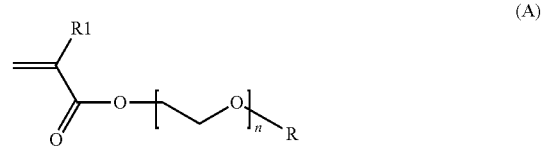

Wherein R1 represents a hydrogen atom or a methyl radical, R represents a linear or branched alkyl radical comprising from eight to thirty carbon atoms and n represents a number greater than or equal to one and less than or equal to fifty. These polymers have very marked thickening properties, in particular in the presence of electrolytes. They function over a wide pH range and make it possible to produce transparent gels. However, formulations with a low pH thickened by some of them do not have satisfactory resistance to salts over the long term and some of them, which contain fatty alcohols, have an unappealing elastic appearance and give sticky sensations to the touch and/or an appearance of a granular and non-continuous cream or emulsion.

The applicant has shown that these drawbacks could be avoided by selecting some of these terpolymers, which had not been disclosed in the French patent application published under the number 2 910 899, and has developed novel branched or cross-linked anionic polyelectrolytes, such as those described in the international application published under the number WO 2011/030044, which result from the radical polymerisation of at least one monomer having a partially salified or completely salified strong acid function, with at least one neutral monomer, and at least one monomer of formula (B):

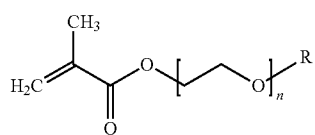

wherein R represents a linear or branched alkyl radical comprising eight to twenty carbon atoms and n represents a number greater than or equal to one and less than or equal to thirty.

The cosmetics and pharmaceutical industries are also seeking galenic forms reducing the risks of skin intolerances, and consequently tend to select ingredients constituting said galenic forms that are well tolerated and also to reduce, in the composition thereof, the proportion of ingredients liable to increase the likelihood of intolerance reactions on the skin. In this regard, the cosmetics and pharmaceutical industries seek to develop oil-in-water emulsions that are devoid of stabilising systems comprising emulsifying surfactants. The terpolymers described in the international application published under the number WO 2011/030044 therefore constitute ideal candidates for preparing oil-in-water emulsions free from emulsifying surfactants.

However, when oil-in-water emulsions are prepared using such synthetic thickening terpolymers in the absence of emulsifying surfactants, the appearance of lumps clusters is observed in said oil-in-water emulsions free from emulsifying surfactants during the storage thereof over time. It is therefore necessary to develop novel oil-in-water emulsions, free from emulsifying surfactants, that do not present during the long-term storage thereof clusters on storage, but which retain a high viscosity in the presence of electrolyte-enriched media and over a wide pH range, as well as satisfactory sensory properties, namely free from a sticky and stringy character on the handling thereof and after application on the skin.

Polysaccharides have been used for many years as agents for modifying texture and/or rheology for preparing food, cosmetic or pharmaceutical compositions. Depending on the chemical constitution thereof, they may be used as gelling agents and/or as thickening agents. Thickening agent means a chemical compound that increases the viscosity of the medium wherein it is introduced. Gelling agent means a compound that transforms a liquid medium into a structured state, which does not flow, by forming a three-dimensional lattice in the liquid; the gel being considered to be an intermediate state between the liquid state and the solid state.

Polysaccharides are polymers of saccharides. The IUPAC definition of saccharides designates sugars, compounds of sugars strictly speaking and derivatives thereof obtained either by reduction of a carbonyl group, or by oxidation of one or more hydroxyl functions, or by replacing one or more hydroxyl functions with a hydrogen atom, an amine group, a phosphate function or a sulfate function.

The polysaccharides most commonly used for preparing food, cosmetic or pharmaceutical compositions mainly consist of sugars, such as glucose, galactose or mannose or sugar derivatives for which the hydroxyl function of the terminal carbon has been oxidised into a carboxyl function. Two distinct groups can be distinguished among polysaccharides: polysaccharides consisting solely of (or poly-sugars) and polysaccharides consisting of sugar derivatives.

Among the polysaccharides consisting only of sugars, one may distinguish distinction may be made of glucans, which are homopolymers of glucose which are very plentiful in nature, glucomannoglycans, xyloglycans and galactomannans, which are polymers of which the main chain consists of D-mannose units, interconnected at β-1,4, and whereon D-galactose units are laterally grafted by α-1,6 bonds.

Galactomannans are found in a plurality of plant species, and more particularly in legume species wherein they form the grain albumen. According to the plant origin thereof, the degree of substitution (DS) of the D-galactose units on the primary D-mannose chains of galactomannans varies between 0 and 1:

galactomannans obtained from cassia gum presenting a degree of substitution (DS) of approximately 1/5, signifying lateral grafting of one D-galactose unit every 5 D-mannose units present on the primary polysaccharide chain galactomannans obtained from carob bean gum presenting a degree of substitution (DS) of approximately 1/4, signifying lateral grafting of one D-galactose unit every 4 D-mannose units present on the primary polysaccharide chain galactomannans obtained from tara gum presenting a degree of substitution (DS) of approximately 1/3, signifying lateral grafting of one D-galactose unit every 3 D-mannose units present on the primary polysaccharide chain galactomannans obtained from guar gum presenting a degree of substitution (DS) of approximately 1/2, signifying lateral grafting of one D-galactose unit every 2 D-mannose units present on the primary polysaccharide chain galactomannans obtained from fenugreek gum presenting a degree of substitution (DS) of approximately 1/1, signifying lateral grafting of one D-galactose unit for practically all the D-mannose units present on the primary polysaccharide chain.

As a sub-category of polysaccharides, galactomannans have already been associated with synthetic thickeners resulting from the radical polymerisation of monomers such as acrylic acid, acrylic acid esters, 2-acrylamino 2-methyl propanesulfonic acid and/or the salts thereof, acrylamide, (2-hydroxy ethyl) acrylate.

The American patent published under the number U.S. Pat. No. 4,540,510 describes the preparation of aqueous gels using homopolymers of 2-acrylamido 2-methyl propane sulfonic acid and galactomannans, such as those derived from guar gum and tara gum. However, the aqueous gels which are obtained and used for applications in the field of underground cavity fracturing, or for preparing pigment pastes for printing on textile, or pigment suspension in paints, or in the preparation of cosmetic formulations comprising alcohols as co-solvents, are not suitable for reaching sufficient degrees of viscosity to enable the preparation of oil-in-water emulsions which are enriched with electrolytes and stable during storage.

The French patent application published under the number 2 940 111 describes the use of compositions comprising polysaccharides, suitable for being associated with hydrophilic gelling agents particularly chosen from among copolymers comprising 2-acrylamido-2-methylpropane sulfonic acid and acrylamide as constituent monomers, or comprising 2-acrylamido-2-methylpropane sulfonic acid polyoxyethylenated alkyl methacrylates. These compositions are intended for uses in make-up, having the property of not transferring onto substrates whereon they are placed in contact as well as the property consisting of resisting water after application on the skin. However, the hydrophilic gelling agents described in the French patent application published under the number 2 940 111 are known not to make it possible to reach high levels of viscosity in the presence of media enriched with electrolytes.

The American patent application published under the number US 2011/0274629 A1 describes mixtures of galactomannans and a modified xanthan gum, characterised by a pyruvate content less than 0.5% by weight and the use thereof as thickening agents for preparing cosmetic compositions.

The European patent application published under the number EP 0 152 095 A1 describes compositions comprising homopolymers of 2-acrylamido 2-methylpropane sulfonic acid or 2-methylacrylamido 2-methylpropane sulfonic acid, galactomannans, and the uses thereof as thickening agents of aqueous or alcoholic media, in applications for drilling for oil, preparing printing pastes for textiles, and preparing cosmetic compositions comprising alcohols.

The French patent application published under the number 2 466 273 describes cosmetic emulsions of which the aqueous phase is thickened by natural gums, more particularly galactomannans and even more particularly tara gum.

The inventors have therefore sought to develop novel oil-in-water emulsions, free from emulsifying surfactants in the stabilising system thereof, enriched with salts, retaining a high viscosity and a homogeneous appearance after a prolonged storage period.

For this reason, according to a first aspect, the subject matter of the invention is a composition ($C_1$) presented in the form of an oil-in-water type emulsion, characterised in that it comprises for 100% of the mass thereof:
  5 to 55% by weight, more particularly 7% to 30% by weight, and even more particularly 10% to 20% by weight of an oil phase ($P_1$) consisting of at least one oil and optionally at least one wax,
  0.025% to 3.75% by weight, more particularly 0.125% to 3% by weight, and even more particularly 0.125% to 2.25% by weight of at least one cross-linked anionic polyelectrolyte (PA) resulting from the polymerisation of partially or completely salified 2-methyl 2-[(1-oxo 2-propenyl)amino]1-propane sulfonic acid, with at least one neutral monomer chosen from acrylamide, (2-hydroxy ethyl) acrylate, N,N-dialkyl acrylamides, wherein each of the alkyl groups comprises between one and four carbon atoms, and at least one monomer of formula (I):

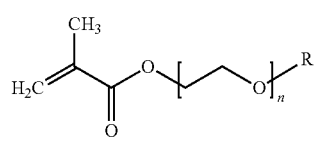

(I)

wherein R represents a linear or branched alkyl radical comprising from eight to twenty carbon atoms and n represents a number greater than or equal to one and less than or equal to twenty, in the presence of at least one cross-linking agent, from 0.025% to 3.75% by weight, more particularly from 0.125% to 3% by weight, and even more particularly from 0.125% to 2.25% by weight of at least one galactomannan (GM) having a degree of substitution (DS) of approximately 1/3, from 37.5% to 94.95% by weight, more particularly 55% to 94.95% by weight, and even more particularly from 65% to 94.95% by weight of a cosmetically acceptable aqueous phase ($P_2$), said aqueous phase ($P_2$) comprising for 100% of the weight thereof from 1% to 25% by weight, more particularly from 1.5% to 15% by weight of at least one salt (S) presented in a dissolved form, said composition ($C_1$) furthermore being characterised in that the ratio by weight between the galactomannan (GM) and the cross-linked anionic polyelectrolyte (PA) is greater than or equal to 1/3 and less than or equal to 3/1, more particularly greater than or equal to 1/2 and less than or equal to 3/2, and even more particularly greater than or equal to 2/3 and less than or equal to 1.

The term oil denotes, in the definition of the composition ($C_1$) subject matter of this invention, a compound and/or a mixture of compounds insoluble in water, and liquid at 25° C., such as that chosen in particular from:
  mineral oils such as paraffin oil, liquid petrolatum, isoparaffins or white mineral oils;
  oils of animal origin, such as squalene or squalane,
  plant oils, such as phytosqualane, sweet almond oil, copra oil, castor oil, jojoba oil, olive oil, rapeseed oil, peanut oil, sunflower oil, wheat germ oil, maize germ oil, soya bean oil, cotton oil, alfalfa oil, poppy oil, pumpkin seed oil, evening primrose oil, millet oil, barley oil, rye oil, safflower oil, candlenut oil, passionflower oil, hazelnut oil, palm oil, shea butter, apricot kernel oil, calophyllum oil, sisymbrium oil, avocado oil, calendula oil, oils derived from flowers or vegetables;
  ethoxylated plant oils;
  synthetic oils such as fatty acid esters such as butyl myristate, propyl myristate, cetyl myristate, isopropyl palmitate, butyl stearate, hexadecyl stearate, isopropyl stearate, octyl stearate, isocetyl stearate, dodecyl oleate, hexyl laurate, propylene glycol dicaprylate, esters derived from lanolic acid, such as isopropyl lanolate, isocetyl lanolate, monoglycerides, diglycerides and triglycerides of fatty acids such as glycerol triheptanoate, alkylbenzanoates, hydrogenated oils, poly(alpha-olefin), polyolefins such as poly(isobutene), synthetic isoalkanes such as isohexadecane, isododecane, perfluorinated oils and
  silicone oils such as dimethylpolysiloxanes, methylphenyl-polysiloxanes, silicones modified by amines, silicones modified by fatty acids, silicones modified by alcohols, silicones modified by alcohols and fatty acids, silicones modified by polyether groups, modified epoxy silicones, silicones modified by fluorinated groups, cyclic silicones and silicones modified by alkyl groups.

The term wax denotes, in the definition of the composition ($C_1$) that is the subject matter of this invention, particularly beeswax, carnauba wax, candelilla wax, ouricury wax, Japan wax, cork fibre wax, sugarcane wax, paraffin waxes, lignite waxes, microcrystalline waxes, lanolin wax; ozokerite; polyethylene wax; silicone waxes; plant waxes; fatty alcohols and fatty acids solid at ambient temperature; glycerides solid at ambient temperature.

The term galactomannan (GM) having a degree of substitution (DS) of approximately 1/3 denotes, in the definition of the composition ($C_1$) that is the subject matter of this invention, a polysaccharide of which the main chain consists of D-mannose units, interconnected at the β-1,4 position, and whereon D-galactose units are laterally grafted by α-1,6 bonds, such that grafting of one D-galactose unit is observed on average every 3 D-mannose units present on the main chain of said polysaccharide. Galactomannan (GM) as defined above is obtained more particularly from tara gum.

Cross-linked anionic polyelectrolyte (PA) means, in the definition of the composition ($C_1$) that is the subject matter of this invention, a non-linear cross-linked anionic polyelectrolyte, presented in the state of a three-dimensional lattice insoluble in water, but swellable in water and leading to the obtaining of a chemical gel.

Partially salified or completely salified means in the definition of the cross-linked anionic polyelectrolyte (PA) present in the composition ($C_1$) as defined above, that said 2-methyl 2-[(1-oxo 2-propenyl)amino]1-propane sulfonic acid is partially or completely salified, in particular in the form of alkaline metal salt, for example in the form of sodium salt or potassium salt, or in the form of ammonium salt.

In the composition ($C_1$) that is the subject matter of this invention, said cross-linked anionic polyelectrolyte (PA) as defined above comprises generally between 5% molar and 95% molar of monomeric units from partially or completely salified 2-methyl-2-[(1-oxo 2-propenyl)amino]1-propane sulfonic acid, more particularly between 10% molar and 90% molar, and quite particularly between 20% molar and 80% molar.

In the composition ($C_1$) that is the subject matter of this invention, said cross-linked anionic polyelectrolyte (PA) as defined above comprises generally between 4.9% molar and 90% molar of monomeric units from at least one of said neutral monomers, more particularly between 9.5% molar and 85% molar, and quite particularly between 15% molar and 75% molar.

According to one particular aspect of this invention, said cross-linked anionic polyelectrolyte (PA) as defined above, comprises generally between 0.1% molar and 10% molar of monomers of formula (I) and more particularly between 0.5% molar and 5% molar.

According to a further particular aspect of this invention, said neutral monomer is more particularly selected from acrylamide, N,N-dimethyl acrylamide, N,N-diethyl acrylamide, N,N-dipropyl acrylamide or (2-hydroxy ethyl) acrylate, in particular from acrylamide, (2-hydroxy ethyl) acrylate or N,N-dimethyl acrylamide and more particularly from (2-hydroxy ethyl) acrylate or N,N-dimethyl acrylamide.

In formula (I) as defined above, linear or branched alkyl radical comprising from eight to twenty carbon atoms means more particularly for R:
either a radical derived from linear primary alcohols such as for example, the octyl, decyl, undecyl, dodecyl, tridecyl, tetradecyl, pentadecyl, hexadecyl, heptadecyl, octadecyl, nondecyl or eicosyl radical;
or a radical derived from Guerbet alcohols, which are branched 1-alkanols complying with the general formula:

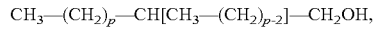

wherein p represents an integer number between 2 and 9, such as, for example, the 2-ethyl hexyl, 2-propyl heptyl, 2-butyl octyl, 2-pentyl nonyl, 2-hexyl decyl or 2-octyl dodecyl radicals;
or a radical derived from isoalkanols complying with the general formula:

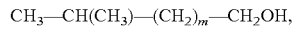

wherein m represents an integer between 2 and 16, such as, for example the 4-methyl pentyl, 5-methyl hexyl, 6-methyl heptyl, 15-methyl pentadecyl or 16-methyl heptadecyl radicals, or the 2-hexyl octyl, 2-octyl decyl or 2-hexyl dodecyl radicals.

According to a particular aspect of the present invention, the subject matter of the invention is a composition ($C_1$) such as defined above, wherein, in the formula (I) as defined above, R represents an alkyl radical comprising 12 to 18 carbon atoms.

According to another particular aspect, the subject matter of the invention is a composition ($C_1$) such as defined above, wherein, in the formula (I) as defined above, n represents an integer number between 3 and 20.

According to an even more particular aspect, the subject matter of the invention is a composition ($C_1$) such as defined above, wherein said monomer of formula (I) is tetraethoxylated lauryl methacrylate, eicosaethoxylated stearyl methacrylate, or ethoxylated behenyl methacrylate having 25 moles of ethylene oxide, and quite particularly tetraethoxylated lauryl methacrylate.

According to another particular aspect, the subject matter of the invention is a composition ($C_1$) such as defined above, wherein said cross-linked anionic polyelectrolyte (PA) is cross-linked with a diethylenic or polyethylenic compound in the molar proportion expressed in relation to the monomers used, of 0.005% to 1%, more particularly 0.01% to 0.5% and quite particularly 0.01% to 0.25%. The cross-linking agent is more particularly chosen from ethylene glycol dimethacrylate, tetraallyloxyethane, ethylene glycol diacrylate, diallyl urea, triallyl amine, trimethylol propanetriacrylate or methylene-bis(acrylamide) or a mixture of these compounds.

The cross-linked anionic polyelectrolyte (PA) used in the composition ($C_1$) such as defined above that is the subject matter of the present invention may also comprise various additives, such as complexing agents, transfer agents or chain-limiting agents.

According to a particular aspect, the subject matter of the invention is a composition ($C_1$) as described above wherein said cross-linked anionic polyelectrolyte (PA) is chosen from:
terpolymers of 2-methyl 2-[(1-oxo 2-propenyl)amino]1-propane sulfonic acid partially salified in the form of ammonium salt, acrylamide and tetraethoxylated methacrylate, cross-linked with trimethylol propanetriacrylate;
terpolymers of 2-methyl 2-[(1-oxo 2-propenyl)amino]1-propane sulfonic acid partially salified in the form of ammonium salt, acrylamide and eicosaethoxylated stearyl methacrylate, cross-linked with trimethylol propanetriacrylate;
terpolymers of 2-methyl 2-[(1-oxo 2-propenyl)amino]1-propane sulfonic acid partially salified in the form of ammonium salt, (2-hydroxy ethyl) acrylate and tetraethoxylated lauryl methacrylate, cross-linked with trimethylol propanetriacrylate;
terpolymers of 2-methyl 2-[(1-oxo 2-propenyl)amino]1-propane sulfonic acid partially salified in the form of ammonium salt, (2-hydroxy ethyl) acrylate and eicosaethoxylated stearyl methacrylate, cross-linked with trimethylol propanetriacrylate;
terpolymers of 2-methyl 2-[(1-oxo 2-propenyl)amino]1-propane sulfonic acid partially salified in the form of ammonium, N,N-dimethyl acrylamide and tetraethoxylated lauryl methacrylate, cross-linked with trimethylol propanetriacrylate; or terpolymers of 2-methyl 2-[(1-oxo 2-propenyl)amino]1-propane sulfonic acid partially salified in the form of ammonium salt, N,N-dimethyl acrylamide and eicosaethoxylated stearyl methacrylate, cross-linked with trimethylol propanetriacrylate.

According to an even more particular aspect, the subject matter of the invention is a composition ($C_1$) as described above wherein said cross-linked anionic polyelectrolyte (PA) is chosen from:

terpolymers of 2-methyl 2-[(1-oxo 2-propenyl)amino]1-propane sulfonic acid partially salified in the form of ammonium salt, N,N-dimethyl acrylamide and tetraethoxylated lauryl methacrylate, cross-linked with trimethylol propanetriacrylate; or terpolymers of 2-methyl 2-[(1-oxo 2-propenyl)amino]1-propane sulfonic acid partially salified in the form of ammonium salt, (2-hydroxy ethyl) acrylate and tetraethoxylated lauryl methacrylate, cross-linked with trimethylol propanetriacrylate.

In the composition ($C_1$) according to the invention, the in situ combination of the cross-linked anionic polyelectrolyte (PA) and galactomannan (GM) having a degree of substitution (DS) of approximately 1/3, as defined above and in the proportions as defined above, constitutes the stabilising system of said composition ($C_1$).

The expression "cosmetically acceptable" used in the definition of the aqueous phase ($P_2$) of the composition ($C_1$) that is the subject matter of this invention, means according to European Economic Community Council Directive No. 76/768/EEC of 27 Jul. 1976 amended by Directive No. 93/35/EEC of 14 Jun. 1993, that said aqueous phase ($P_2$) comprises water and any substance or preparation intended to be placed in contact with the various parts of the human body (epidermis, pilous and hair system, nails, lips and genital organs) or with the teeth and the mucous membranes of the oral cavity with a view exclusively and mainly to cleansing them, perfuming them, modifying the appearance thereof and/or correcting the body odours thereof and/or protecting them or keeping them in good condition.

A cosmetically acceptable aqueous phase ($P_2$) included in the composition ($C_1$) that is the subject matter of this invention contains water, and may conventionally contain one or a plurality of cosmetically acceptable water-soluble organic solvents, a mixture of water and one or a plurality of cosmetically acceptable organic solvents. The cosmetically acceptable solvents may more particularly be chosen from the polyhydric alcohols such as for example glycerol, diglycerol, triglycerol, glycerol oligomers, xylitol, erythritol, sorbitol, 2-methyl propanediol-1,3; alkoxylated polyhydric alcohols; glycols, such as for example butylene glycol, hexylene glycol, caprylyl glycol or 1,2-octanediol or 1,2-pentanediol, pentylene glycol, monopropylene glycol, dipropylene glycol, isoprene glycol, butyl diglycol, polyethylene glycols of which the molecular weight is between 200 g·mol$^{-1}$ and 8000 g·mol$^{-1}$; or water-soluble alcohols such as for example ethanol, isopropanol or butanol.

In the composition ($C_1$) as defined above, salt (S) means a heteropolar compound the crystalline lattice of which comprises the participation of at least one type of cation different to the hydrogen ion and at least one type of anion different to the hydroxide ion.

According to a particular aspect, the salt (S) presented in dissolved form in the aqueous phase ($P_2$) of the composition ($C_1$) that is the subject matter of this invention is selected from inorganic salts or from organic salts.

According to a more particular aspect, the salt (S) is particularly selected from inorganic salts and it consists in particular of a cation that is the ammonium ion or a metal cation and an anion selected from the elements of the group consisting of the halides, carbonates, bicarbonates, phosphate, nitrates, borates and sulfates.

According to a more particular aspect, the subject matter of this invention is a composition ($C_1$) as defined above characterised in that the salt (S) is an inorganic salt the metal cation of which is a monovalent or multivalent cation chosen from the elements of the group consisting of the sodium, potassium, lithium, calcium, magnesium, zinc, manganese, iron, copper, cobalt, silver, gold, aluminium, barium, bismuth, selenium, zirconium, strontium and tin cations.

According to an even more particular aspect, the subject matter of the invention is a composition ($C_1$), as defined above, characterised in that the salt (S) is an inorganic salt chosen from the elements of the group consists of sodium chloride, calcium chloride, magnesium chloride, calcium sulfate, ammonium sulfate, calcium carbonate, zinc sulfate, magnesium sulfate, sodium borate.

According to another particular aspect, the salt (S) is particularly selected from the organic salts.

According to a particular aspect, the subject matter of the invention is a composition ($C_1$) as defined above, characterised in that the salt (S) is an organic salt consisting of a cation which is the ammonium ion or a metal cation and an organic anion that is an organic compound having at least one carboxylic acid function in carboxylate form or at least one sulfonic acid function in sulfonate form or at least one sulfate function.

According to this particular aspect, the subject matter of the invention is a composition ($C_1$), as defined above, characterised in that the salt (S) is an organic salt consisting of a monovalent or multivalent metal cation more particularly chosen from the elements of the group consisting of the sodium, potassium, lithium, calcium, magnesium, zinc, manganese, iron, copper, cobalt, silver, gold, aluminium, barium, bismuth, selenium, zirconium, strontium and tin cations. According to this particular aspect, the salt (S) is an organic salt consisting of the cation chosen from the elements of the group consisting of the sodium, calcium, magnesium, zinc and manganese cations, and even more particularly, the salt (S) is an organic salt consisting of the sodium cation.

According to a particular aspect, the subject matter of the invention is a composition ($C_1$), as defined above characterised in that the salt (S) is an organic salt consisting of a cation that is the ammonium ion or a metal cation as described above, and an organic anion that is an organic compound having at least one carboxylic function in carboxylate form chosen from the elements of the group consisting of glycolic acid, citric acid, tartaric acid, salicylic acid, lactic acid, mandelic acid, ascorbic acid, pyruvic acid, fumaric acid, retinoic acid, benzoic acid, kojic acid, malic acid, gluconic acid, galacturonic acid, propionic acid, heptanoic acid, 4-amino benzoic acid, cinnamic acid, benzalmalonic acid, aspartic acid and glutamic acid.

According to an even more particular aspect, the subject matter of the invention is a composition ($C_1$), as defined above characterised in that the salt (S) is an organic salt selected from the elements of the group consisting of sodium glycolate, sodium citrate, sodium salicylate, sodium lactate, sodium gluconate, zinc gluconate, manganese gluconate, copper gluconate and magnesium aspartate.

According to another particular aspect, the subject matter of the invention is a composition ($C_1$), as defined above characterised in that the salt (S) is an organic salt consisting of a cation that is the ammonium ion or a metal cation as described above, and an organic anion that is an organic compound having at least one sulfonic acid function in sulfonate form chosen from the elements of the group consisting of 2-phenylbenzimidazole-5-sulfonic acid, the sulfonic acids derived from benzophenones, such as for example 4-hydroxy-2-methoxy-5-(oxo-phenylmethyl)benzene sulfonic acid (said acid being registered under the name Benzophenone-4), sulfonic acids derived from 3-benzylidene camphor such as for example 4-(2-oxo-3-bornylidenemethyl)benzene sulfonic acid, 2-methyl-5 (2-oxo-3-bornylidenemethyl)benzene sulfonic acid.

According to an even more particular aspect, the subject matter of the invention is a composition ($C_1$), as defined above characterised in that the salt (S) is an organic salt selected from the elements of the group consisting of sodium 2-phenylbenzimidazole-5-sulfonate and sodium 4-hydroxy 2-methoxy 5-(oxo-phenylmethyl)benzene sulfonate. 2-phenylbenzimidazole-5-sulfonic acid is marketed in particular under the brand name EUSOLEX™ 232 by the company Merck. Sodium 4-hydroxy-2-methoxy-5-(oxo-phenylmethyl)benzene sulfonate is registered under the name benzophenone-5.

In general terms, the composition ($C_1$) that is the subject matter of this invention comprises, in addition to said oil phase ($P_1$), the stabilising system, composed of the in situ combination of the cross-linked anionic polyelectrolyte (PA) and galactomannan (GM) as defined above, and said cosmetically acceptable aqueous phase ($P_2$), adjuvants and/or additives routinely used in the field of cosmetic, dermocosmetic, pharmaceutical or dermopharmaceutical formulations.

Among the adjuvants likely to be present in said composition ($C_1$) include film-forming compounds, hydrotropic agents, plasticizing agents, opacifying agents, pearlescent agents, superfatting agents, sequestering agents, chelating agents, non-ionic detergent surfactants, antioxidant agents, perfumes, preservatives, conditioning agents, bleaching agents intended for decolouring hair and skin, active ingredients intended to provide a treating action vis-à-vis the skin or hair, mineral fillers or pigments, particles procuring a visual effect or intended for encapsulating active ingredients, exfoliating particles, texture agents, optical brighteners, insect repellents.

The opacifying and/or pearlescent agents include for example sodium or magnesium palmitates, stearates or hydroxystearates, ethylene glycol or polyethylene glycol monostearates or distearates, fatty alcohols, styrene homopolymers and copolymers such as styrene acrylate copolymer marketed under the name MONTOPOL™ OP1 by SEPPIC.

Among the texture agents that can be associated with said composition ($C_1$), mention may be made of N-acyl amino acids, such as lauroyl lysine marketed under the name AMINOHOPE™ LL by the company AJINOMOTO, starch octenyl succinate marketed under the name DRYFLO™ by the company NATIONAL STARCH, myristyl polyglycoside marketed by SEPPIC under the name MONTANOV™ 14, cellulose fibres, cotton fibres, chitosan fibres, talc, sericite, mica.

Among the active ingredients that can be associated with said composition ($C_1$), mention may be made for example of vitamins and derivatives thereof, in particular the esters thereof, such as retinol (vitamin A), and the esters thereof (retinyl palmitate for example). ascorbic acid (vitamin C) and the esters thereof, ascorbic acid sugar derivatives (such as for example ascorbyl glucoside), tocopherol (vitamin E) and the esters thereof (such as for example tocopherol acetate), vitamins B3 or B10 (niacinamide and derivatives thereof); the compounds showing a skin lightening or depigmenting action such as for example SEPIWHITE™ MSH, arbutin, kojic acid, hydroquinone, VEGEWHITE™, GATULINE™, SYNERLIGHT™, BIOWHITE™, PHYTOLIGHT™, DERMALIGHT™, CLARISKIN™, MELASLOW™, DERMAWHITE™, ETIOLINE, MELAREST™, GIGAWHITE™, ALBATINE™, LUMISKIN™; the compounds showing a calming action such as SEPICALM™ S, allantoin and bisabolol; anti-inflammatory agents; compounds showing a moisturising action such as for example urea, hydroxyureas, glycerol, polyglycerols, AQUAXYL™, glycerolglucoside; polyphenol extracts such as for example grape extracts, pine extracts, wine extracts, olive extracts; compounds exhibiting a slimming or lipolytic action such as caffeine or derivatives thereof, ADIPOSLIM™, ADIPOLESS™; N-acylated proteins; N-acylated peptides such as for example MATRIXIL™; N-acylated amino acids; partial hydrolysates of N-acylated proteins; amino acids; peptides; total protein hydrolysates; soya bean extracts, for example Raffermine™; wheat extracts, for example TENSINE™ or GLIADINE™; plant extracts, such as plant extracts enriched in tannins, —plant extracts enriched in isoflavones or—plant extracts enriched in terpenes, fresh or sea water alga extracts; marine extracts in general such as corals; essential waxes; bacterial extracts; ceramides; phospholipids; compounds showing an antimicrobial action or a purifying action, such as for example LIPACIDE™ C8G, LIPACIDE™ UG, SEPICONTROL™ A5; OCTOPIROX™ or SENSIVA™ SC50; the compounds exhibiting an energising or tonic property such as Physiogenyl™, panthenol and derivatives thereof such as SEPICAP™ MP; anti-aging agents such as SEPILIFT™ DPHP, LIPACIDE™ PVB, SEPIVINOL™, SEPIVITAL™, MANOLIVA™, PHYTO-AGE™, TIMECODE™; SURVICODE™; anti-photoaging agents; agents protecting the integrity of the dermo-epidermic junction; agents increasing the synthesis of components of the extracellular matrix such as for example collagen, elastins, glycosaminoglycans; agents promoting chemical cell communication such as cytokines or physical cell communication such as integrins; agents creating a "warming" sensation on the skin such as skin microcirculation activators (such as for example nicotinic acid derivatives) or products creating a "cooling" sensation on the skin (such as for example menthol and derivatives); agents improving skin microcirculation, for example venotonics; draining agents; agents for decongestant purposes such as for example extracts of *gingko biloba*, ivy, horse chestnut, bamboo, ruscus, butcher's broom, *centella asiatica*, fucus, rosemary and willow.

Among the active ingredients that may be associated with said composition ($C_1$), mention may more particularly be made of skin tanning or browning agents, such as for example dihydroxyacetone, isatin, alloxan, ninhydrin, glyceraldehyde, mesotartaric aldehyde, gluteraldehyde, erythrulose.

Among the detergent surfactants that may be associated with said composition ($C_1$), mention may be made of fatty alcohol ethoxylated derivatives comprising 8 to 12 carbon atoms, fatty acid ethoxylated derivatives comprising 8 to 12 carbon atoms, fatty ester ethoxylated derivatives comprising 8 to 12 carbon atoms, monoglyceride ethyoxylated derivatives comprising 8 to 12 carbon atoms, alkylpolyglycosides of formula (II);

$$R_2\text{—O(S)}_y\text{—H} \quad \text{(II)}$$

wherein y represents a decimal number between 1 and 5, S represents a reducing sugar residue and $R_2$ represents a saturated or unsaturated, linear or branched alkyl radical, having 5 to 16 carbon atoms, preferably 8 to 14 carbon atoms, or a mixture of compounds of formula (II).

The non-ionic detergent surfactants that can be associated with said composition ($C_1$) are more particularly chosen from the elements of the group consisting of caprylyl capryl glucosides, marketed in particular under the brand name ORAMIX™ CG 110 by the company SEPPIC, decylglucoside, marketed in particular under the brand name ORAMIX™ NS 10 by the company SEPPIC.

Among the pigments that can be associated with said composition ($C_1$), mention may be made of titanium dioxide, brown iron oxides, yellow iron oxides, black iron oxides, or red iron oxides or white or coloured pearlescent pigments such as Mica-Titanium.

Among the sun filters that can be associated with said composition ($C_1$), mention may be made of all those featuring in the amended cosmetics directive 76/768/EEC annex VII, such as for example titanium dioxide, zinc oxide, cinnamic acid esters such as for example 2-ethyl hexyl 4-methoxy cinnamate, isopentyl 4-methoxy cinnamate, non-ionic benzophenone derivatives, 4-amino benzoic acid esters such as for example 2-ethyl hexyl 4-(dimethylamino)benzoate, amyl 4-(dimethylamino)benzoate.

According to another particular aspect, the subject matter of the invention is a composition ($C_1$) as defined above, characterised in that the dynamic viscosity thereof measured at a temperature of 20° C., by means of a Brookfield type viscometer is greater than or equal to 30,000 mPa·s and less than or equal to 200,000 mPa·s, more particularly greater than or equal to 40,000 mPa·s and less than or equal to 130,000 mPa·s and even more particularly greater than or equal to 50,000 mPa·s and less than or equal to 130,000 mPa·s.

When the dynamic viscosity of the composition ($C_1$) is less than or equal to approximately 100,000 mPa·s at a temperature of 20° C., said dynamic viscosity is measured by means of a Brookfield LVT type viscometer at a speed of 6 revolutions per minute.

When the dynamic viscosity of the composition ($C_1$) is greater than approximately 100,000 mPa·s at a temperature of 20° C., said dynamic viscosity is measured using a Brookfield RVT type viscometer at a speed of 5 revolutions per minute.

According to one particular aspect, the subject matter of the invention is a composition ($C_1$) as defined above, characterised in that the conductivity of said composition ($C_1$) measured at a temperature of 20° C. by means of an LF 196 brand conductimeter by the company WTW equipped with a Tetracon 96 electrode, is greater than or equal to 15 millisiemens·cm$^{-1}$ (mS·cm$^{-1}$) and less than or equal to 200 mS·cm$^{-1}$, more particularly greater than or equal to 15 mS·cm$^{-1}$ and less than or equal to 150 mS·cm$^{-1}$.

Said composition ($C_1$) is presented in particular in the form of a continuous aqueous phase emulsion or microemulsion.

When said composition ($C_1$) has suitable fluidity characteristics, it may also be used for impregnating substrates consisting of synthetic or natural textile fibres, woven or non-woven, or paper, to form articles, such as for example wipes, intended for care, protection or cleansing of the skin, scalp or hair, or such as for example papers for sanitary or household use.

Said composition ($C_1$) can be used by application on the skin, mucosa, hair or scalp, whether it consists of a direct application in the case of a cosmetic, dermocosmetic, dermopharmaceutical or pharmaceutical composition, or an indirect application in the case of a product for care, protection, cleansing of the body presented in the form of a textile article, such as for example a wipe, or a paper article, such as for example paper for sanitary use, intended to be in contact with the skin, hair or scalp.

The composition ($C_1$) as defined above that is the subject matter of this invention is stable over time after a storage period of at least one month at 20° C. and retains a homogeneous appearance, not showing the appearance of lumps or clusters, after the same storage period under the same experimental conditions, without it being necessary to incorporate emulsifying surfactants into said composition ($C_1$).

According to a particular aspect, the subject matter of the present invention is a composition ($C_1$) comprising for 100% of the weight thereof a quantity of 0% by weight of emulsifying surfactants (EM) selected from the elements of the group ($G_1$) consisting of:
  fatty acids comprising 14 to 22 carbon atoms,
  ethoxylated fatty acids comprising 14 to 22 carbon atoms,
  fatty acid esters comprising 14 to 22 carbon atoms,
  fatty acid esters comprising 14 to 22 carbon atoms and polyglycerol,
  fatty alcohols comprising 14 to 22 ethoxylated carbon atoms,
  fatty acid esters comprising 14 to 22 carbon atoms and sucrose,
  alkylpolyglycosides of formula (III):

$$R_3\text{—O—}(S)_z\text{—H} \tag{III}$$

wherein z represents a decimal number between 1 and 5, S represents a reducing sugar residue and $R_3$ represents a saturated or unsaturated, linear or branched alkyl radical, having 14 to 22 carbon atoms, preferably 16 to 22 carbon atoms, or a mixture of compounds of formula (III).

In the definition of formula (III) as defined above, z is a decimal number representing the mean degree of polymerisation of the residue S. When z is an integer number, $(S)_z$ is the rank z polymeric residue of the residue S. When z is a decimal number, the formula (III) represents a mixture of compounds:

$$a_1R_3\text{—O—S—H}+a_2R_2\text{—O—}(S)2\text{-H}+a_3R_3\text{—O—}(S)_3\text{—H}+\ldots+a_gR_3\text{—O—}(S)_q\text{—H}$$

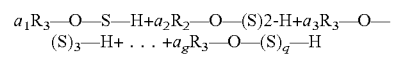

with q representing an integer number between 1 and 10 and in the molar proportions $a_1, a_2, a_3 \ldots a_g$ such that:
g=1

$\Sigma a_g = 1; a_1 > 0$ g=10

In formula (III) as defined above, z is between 1.05 and 5.0 and more particularly between 1.05 and 2.

In formula (III) as defined above, $R_3$ represents for example the n-tetradecyl radical, the n-hexadecyl radical, the n-octadecyl radical, the n-eicosyl radical or the n-dodecosyl radical.

Reducing sugar means, in the definition of formula (III), the saccharide derivatives that do not have in the structures thereof, a glycoside bond established between an anomeric carbon and the oxygen of an acetal group as defined in the reference publication "Biochemistry", Daniel Voet/Judith G. Voet, p. 250, John Wyley & Sons, 1990. The oligomeric structure $(S)_z$, may be presented in any form of isomerism, whether it consists of optical isomerism, geometric isomerism or positional isomerism; it may also represent a mixture of isomers.

In formula (III) as defined above, the group $R_3$—O— is bound to S by the anomeric carbon of the saccharide residue, so as to form an acetal function.

In formula (III) as defined above, S represents a reducing sugar residue chosen from glucose, xylose or arabinose.

According to a further particular aspect, the subject matter of the present invention is a composition ($C_1$) comprising for 100% of the weight thereof 0.1% to 10% by weight, more particularly 0.1% to 5% by weight, and even more particularly 0.5% to 3% by weight of at least one emulsifying surfactant (EM) selected form the elements of the group ($G_1$) as defined above.

According to this further particular aspect, the ratio by weight between the sum of the quantity by weight of anionic polyelectrolyte (PA) and the quantity by weight of galactomannan (GM), as defined above, and the quantity by weight of the emulsifying agent (EM) is greater than or equal to 1.0, more particularly greater than or equal to 5.0, and even more particularly greater than or equal to 10.0.

According to another aspect, the subject matter of the present invention is a method for preparing the composition ($C_1$) as defined above, comprising:

at least one step a) for preparing a phase ($P'_1$) by mixing cross-linked anionic polyelectrolyte (PA) and galactomannan (GM) in the oil phase ($P_1$); and at least one step b) for emulsifying said phase ($P'_1$) obtained following step a) with the cosmetically acceptable aqueous phase ($P_2$).

In the method that is the subject matter of the invention, the oil phase ($P_1$) comprises one or a plurality of oils and/or one or a plurality of waxes as defined above.

In the case where the oil phase ($P_1$) does not consist of a single oil or a single wax, the oil phase ($P_1$) is prepared by mixing the constituent ingredients thereof at a temperature typically between 20° C. and 85° C., and even more particularly at a temperature between 20° C. and 60° C., and by means of any mixing device known to those skilled in the art, such as for example by means of a mechanical stirring device equipped with an "anchor" type mobile assembly, at stirring speeds between 50 revolutions per minute and 500 revolutions per minute, more particularly between 50 revolutions per minute and 300 revolutions per minute.

In the method that is the subject matter of that is the subject matter of the invention as described above, step a) for preparing a phase ($P'_1$) by mixing cross-linked anionic polyelectrolyte (PA) and galactomannan (GM) in the oil phase ($P_1$) can advantageously be implemented at a temperature less than or equal to 85° C. and greater than or equal to 20° C., more particularly at a temperature less than or equal to 60° C. and greater than or equal to 20° C.

In the method that is the subject matter of that is the subject matter of the invention as described above, step a) for preparing a phase ($P'_1$) by mixing cross-linked anionic polyelectrolyte (PA) and galactomannan (GM) in the oil phase ($P_1$) can be performed by means of any mixing device known to persons skilled in the art, such as for example by means of a mechanical stirring device equipped with an "anchor" type mobile assembly, at stirring speeds between 50 revolutions per minute and 500 revolutions per minute, more particularly between 50 revolutions per minute and 300 revolutions per minute, and such as for example by means of a rotor-stator type stirring device at stirring speeds between 100 revolutions per minute and 10,000 revolutions per minute, more particularly between 500 revolutions per minute and 4000 revolutions per minute.

In the method that is the subject matter of the invention, step b) for emulsifying said phase ($P'_1$) obtained following step a) with the aqueous phase ($P_2$) can advantageously be implemented at a temperature between 20° C. and 90° C., more particularly at a temperature between 20° C. and 85° C., and even more particularly at a temperature between 20° C. and 60°.

In the method that is the subject matter of the invention, for emulsifying said phase ($P'_1$) obtained following step a) with the aqueous phase ($P_2$) may be performed by means of any mixing device known to persons skilled in the art, such as for example by means of a mechanical stirring device equipped with an "anchor" type mobile assembly, at stirring speeds between 50 revolutions per minute and 500 revolutions per minute, more particularly between 50 revolutions per minute and 300 revolutions per minute, and such as for example by means of a rotor-stator type stirring device at stirring speeds between 100 revolutions per minute and 10,000 revolutions per minute, more particularly between 500 revolutions per minute and 4000 revolutions per minute.

In the method that is the subject matter of the invention as described above, the cosmetically acceptable aqueous phase ($P_2$) comprises water, and optionally one or a plurality of cosmetically acceptable organic solvents as described above, and from 1% to 25% by weight, for 100% of the weight of said cosmetically acceptable aqueous phase ($P_2$) of at least one salt (S) presented in a dissolved form and as defined above.

The cosmetically acceptable aqueous phase ($P_2$) is prepared by mixing water, and optionally one or a plurality of cosmetically acceptable organic solvents, with at least one salt (S) as described above, at a temperature between 20° C. and 85° C., and even more particularly at a temperature between 20° C. and 60° C., and by means of any mixing device known to those skilled in the art, such as for example by means of a mechanical stirring device equipped with an "anchor" type mobile assembly, at stirring speeds between 50 revolutions per minute and 500 revolutions per minute, more particularly between 50 revolutions per minute and 300 revolutions per minute.

According to another aspect the subject matter of the present invention is the cosmetic use of the composition ($C_1$) as defined above for cleansing, protecting and/or care of the skin, hair, scalp or mucosa.

Within the scope of the present invention, "cosmetic use" means uses of the composition ($C_1$) intended to improve and/or preserve the external aesthetic appearance of the skin, hair, scalp or mucosa.

According to a more particular aspect, said composition ($C_1$) may be used for cleansing the skin, mucosa, hair or scalp, and more particularly may be used as a bath or shower gel, as a shampoo. In this particular use, it further comprises at least one non-ionic detergent surfactant as described above.

According to another more particular aspect, said composition ($C_1$) can be used for caring for or protecting the skin, such as for example as a cream, milk or lotion for caring for or protecting the face, hands and body.

According to this particular aspect, said composition ($C_1$) can also be used more particularly as a product for protecting the skin against the rays of the sun, as a skin makeup product, as a product protecting the skin against skin aging, as a skin moisturising product, as a product for the cosmetic treatment of acne and/or blackheads and/or comedones.

The experimental report hereinafter illustrates the invention, without limiting the invention.

1.1 Preparation of a Terpolymer of Ammonium 2-methyl 2-[(1-oxo 2-propenyl)amino]1-propane sulfonate, N—N-dimethyl acrylamide and Tetraoxylated Lauryl Methacrylate [AMPSNH$_4$/DMAM/MAL(4OE) 77.4/19.2/3.4 Molar], Cross-Linked with Trimethylol Panetriacrylate (TMPTA) [Example According to the Invention]

592 g of an aqueous solution containing 15% by weight of ammonium 2-methyl 2-[(1-oxo 2-propenyl)amino]1-propane sulfonate (AMPSNH$_4$) in a tert-butanol/water mixture (97.5/2.5 by volume), 10.1 g of N—N-dimethyl acrylamide (DMAM), 4.2 g of tetraethoxylated lauryl methacrylate [MAL(4OE)] and 0.75 g of TMPTA are loaded into a reactor maintained at 25° C. under stirring.

After sufficient time to achieve satisfactory homogenisation of the solution, the solution is deoxygenated by bubbling nitrogen heated to 70° C. 0.42 g of dilauroyl peroxide is then added and the reaction medium is then maintained for approximately 60 minutes at 70° C. and 2 hours at 80° C.

After cooling, the powder that formed during polymerisation is filtered and dried to obtain the required product, hereinafter referred to as: "Polyelectrolyte PA$_1$".

1-2: Preparation of a Terpolymer of Ammonium 2-methyl 2-[(1-oxo 2-propenyl)amino]1-propane sulfonate, (2-hydroxy ethyl) acrylate and Tetraoxylated Lauryl Methacrylate [AMPSNH$_4$/HEA/MAL(4OE) 77.4/19.2/3.4 Molar], Cross-Linked with (TMPTA) [Example According to the Invention]

Using the operating conditions of the method described in paragraph 1.1 above, the quantity required by weight of an aqueous solution containing 15% by weight of AMPSNH$_4$ in a tert-butanol/water mixture (97.5/2.5 by volume) so as to introduce 77.4 molar equivalents of AMPSNH$_4$, the quantity required by weight of (2-hydroxy ethyl) acrylate (HEA) so as to introduce 19.2 molar equivalents of HEA, the quantity required by weight of [MAL(4OE) so as to introduce 3.4 molar equivalents of [MAL(4OE)], and the quantity required by weight of TMPTA so as to obtain the same molar proportion of TMPTA as in paragraph 1-1 are loaded into a reactor maintained at 25° C. under stirring.

After sufficient time to achieve satisfactory homogenisation of the solution, the solution is deoxygenated by bubbling nitrogen heated to 70° C. 0.42 g of dilauroyl peroxide is then added and the reaction medium is then maintained for approximately 60 minutes at 70° C. and 2 hours at 80° C.

After cooling, the powder that formed during polymerisation, is filtered and dried to obtain the required product, hereinafter referred to as: "Polyelectrolyte PA$_2$".

1-3: Preparation of a Copolymer of Ammonium 2-methyl 2-[(1-oxo 2-propenyl)amino]1-propane sulfonate and Tetraoxylated Lauryl Methacrylate [AMPS/MAL(4OE) 95/5 Molar], Cross-Linked with TMPTA [Comparative Example]

Using the operating conditions of the method described in paragraph 1.1 above, the quantity required by weight of an aqueous solution containing 15% by weight of AMPSNH$_4$ in a tert-butanol/water mixture (97.5/2.5 by volume) so as to introduce 95 molar equivalents of AMPSNH$_4$, the quantity required by weight of [MAL(4OE)] so as to introduce 5 molar equivalents of [MAL(4OE)], and the quantity required by weight of TMPTA so as to obtain the same molar proportion of TMPTA as in paragraph 1-1 are loaded into a reactor maintained at 25° C. under stirring.

After a sufficient time to achieve satisfactory homogenisation of the solution, the solution is deoxygenated by bubbling nitrogen heated to 70° C. 0.42 g of dilauroyl peroxide is then added and the reaction medium is then maintained for approximately 60 minutes at 70° C. and 2 hours at 80° C.

After cooling, the powder that formed during polymerisation, is filtered and dried to obtain the required product, hereinafter referred to as: "Polyelectrolyte PA$_3$".

1-4: Preparation of a Copolymer of 2-methyl 2-[(1-oxo 2-propenyl)amino]1-propane sulfonate and (2-hydroxy ethyl) acrylate [AMPS/HEA 90/10 Molar], Cross-Linked with TMPTA [Comparative Example]

Using the operating conditions of the method described in paragraph 1.1 above, the quantity required by weight of an aqueous solution containing 15% by weight of AMPSNH$_4$ in a tert-butanol/water mixture (97.5/2.5 by volume) so as to introduce 90 molar equivalents of AMPSNH$_4$, the quantity required by weight of HEA so as to introduce 10 molar equivalents of HEA, and the quantity required by weight of TMPTA so as to obtain the same molar proportion of TMPTA as in paragraph 1-1 are loaded into a reactor maintained at 25° C. under stirring.

After a sufficient time to achieve satisfactory homogenisation of the solution, the solution is deoxygenated by bubbling nitrogen heated to 70° C. 0.42 g of dilauroyl peroxide is then added and the reaction medium is then maintained for approximately 60 minutes at 70° C. and 2 hours at 80° C.

After cooling, the powder that formed during polymerisation is filtered and dried to obtain the required product, hereinafter referred to as: "Polyelectrolyte PA$_4$".

2-1: Preparation of Oil-in-Water Emulsions According to the Invention

Thirteen oil-in-water emulsions according to the invention, referenced ($E_1$) to ($E_{13}$), of which the proportions by weight of the constituents thereof are recorded in table 1 below, are prepared using the following method:
- in a first beaker, at a temperature of 20° C., one of the polyelectrolytes PA$_1$ or PA$_2$ and Tara gum are dispersed progressively and successively in an oil phase under mechanical stirring at 80 revolutions per minute;
- in a second beaker, at a temperature of 20° C., the aqueous phase comprising the water and the quantity by weight of salt required is prepared;
- the content of the first beaker is progressively poured into the second beaker at a temperature of 20° C., under mechanical stirring by means of a deflocculator at 1200 revolutions per minute;
- the mixture obtained is maintained under stirring for 10 minutes, then drained to obtain the oil-in-water emulsions ($E_1$) to ($E_{13}$).

TABLE 1

| Emulsion | ($E_1$) | ($E_2$) | ($E_3$) | ($E_4$) | ($E_5$) | ($E_6$) |
|---|---|---|---|---|---|---|
| Oil phase: | | | | | | |
| C8-C10 Triglycerides | 15% | 15% | 15% | 15% | 15% | 15% |
| Stabilising system: | | | | | | |
| Polyelectrolyte ($PA_1$) | 1% | 1% | 1% | 1% | 1% | 1.25% |
| Tara gum [2] | 1% | 1% | 1% | 1% | 1% | 0.75% |
| Aqueous phase: | | | | | | |
| Water | Qs 100% | Qs 100% | Qs 100% | Qs 100% | Qs 100% | Qs 100% |
| Sodium chloride | 2% | 4% | 6% | 8% | 10% | 2% |
| Geogard™ 221[1] | 0.6% | 0.6% | 0.6% | 0.6% | 0.6% | 0.6% |

| Emulsion | ($E_7$) | ($E_8$) | ($E_9$) | ($E_{10}$) | ($E_{11}$) |
|---|---|---|---|---|---|
| Oil phase: | | | | | |
| C8-C10 Triglycerides | 15% | 15% | 15% | 15% | 15% |
| Stabilising system: | | | | | |
| Polyelectrolyte ($PA_1$) | 1.25% | 1.25% | 0.5% | 0.5% | 0.5% |
| Tara gum [2] | 0.75% | 0.75% | 1.50% | 1.50% | 1.50% |
| Aqueous phase: | | | | | |
| Water | Qs 100% | Qs 100% | Qs 100% | Qs 100% | Qs 100% |
| Sodium chloride | 4% | 10% | 4% | 10% | 4% |
| Geogard™ 221[1] | 0.6% | 0.6% | 0.6% | 0.6% | 0.6% |

| Emulsion | ($E_{12}$) | ($E_{13}$) |
|---|---|---|
| Oil phase: | | |
| C8-C10 Triglycerides | 15% | 15% |
| Stabilising system: | | |
| Polyelectrolyte ($PA_1$) | 1% | 1% |
| Tara gum [2] | 1% | 1% |
| Aqueous phase: | | |
| Water | Qs 100% | Qs 100% |
| Sodium chloride | 2% | 10% |
| Geogard™ 221[1] | 0.6% | 0.6% |

[1] Geogard™ 221 is a mixture of dehydroacetic acid and benzyl alcohol used as a preservative and marketed by the company LONZA.
[2] Tara gum (CAS number: 39300-88-4) is marketed under the name "Tara gum" by the company Starlight.

2-2: Preparation of Oil-in-Water Emulsions According to the Prior Art

Ten oil-in-water emulsions, referenced ($F_1$) to ($F_{10}$), of which the proportions by weight of the constituents thereof are recorded in table 2 below, are prepared using the following method:

- in a first beaker, at a temperature of 20° C., one of the polyelectrolytes $PA_1$ or $PA_2$ and Tara gum are dispersed progressively and successively in an oil phase under mechanical stirring at 80 revolutions per minute;
- in a second beaker, at a temperature of 20° C., the aqueous phase comprising the water and the quantity by weight of salt required is prepared;
- the content of the first beaker is progressively poured into the second beaker at a temperature of 20° C., under mechanical stirring by means of a deflocculator at 1200 revolutions per minute;
- the mixture obtained is maintained under stirring for 10 minutes, then drained to obtain the oil-in-water emulsions ($F_1$) to ($F_{10}$).

TABLE 2

| | Emulsion | | | | |
|---|---|---|---|---|---|
| | ($F_1$) | ($F_2$) | ($F_3$) | ($F_4$) | ($F_5$) |
| Oil phase: | | | | | |
| C8-C10 Triglycerides | 15% | 15% | 15% | 15% | 15% |
| Stabilising system: | | | | | |
| Polyelectrolyte ($PA_1$) | 1% | 2% | 2% | 0% | 1.25% |
| Tara gum | 1% | 0% | 0% | 2% | 0.75% |
| Aqueous phase: | | | | | |
| Water | Qs 100% | Qs 100% | Qs 100% | Qs 100% | Qs 100% |
| Sodium chloride | 0% | 2% | 4% | 4% | 0% |
| Geogard™ 221 | 0.6% | 0.6% | 0.6% | 0.6% | 0.6% |

| | Emulsion | | | | |
|---|---|---|---|---|---|
| | ($F_6$) | ($F_7$) | ($F_8$) | ($F_9$) | ($F_{10}$) |
| Oil phase: | | | | | |
| C8-C10 Triglycerides | 15% | 15% | 15% | 15% | 15% |
| Stabilising system: | | | | | |
| Polyelectrolyte ($PA_1$) | 0.5% | 0% | 0% | 0% | 0% |
| Polyelectrolyte ($PA_3$) | 0% | 1% | 1% | 0% | 0% |
| Polyelectrolyte ($PA_4$) | 0% | 0% | 0% | 1% | 1% |
| Tara gum | 1.50% | 1% | 1% | 1% | 1% |
| Aqueous phase: | | | | | |
| Water | Qs 100% | Qs 100% | Qs 100% | Qs 100% | Qs 100% |
| Sodium chloride | 0% | 2% | 10% | 2% | 10% |
| Geogard™ 221[1] | 0.6% | 0.6% | 0.6% | 0.6% | 0.6% |

2-3: Demonstration of the Properties and Characteristics of the Oil-in-Water Emulsions According to the Invention Compared to Oil-in-Water Emulsions According to the Prior Art The oil-in-water emulsions ($E_1$) to ($E_{13}$) according to the invention and the oil-in-water emulsions ($F_1$) to ($F_{10}$) according to the prior art prepared in this way, are then stored in an insulated climatic chamber regulated at a temperature of 20° C. for 7 days. After this 7-day period and for each oil-in-water emulsion:

- the visual appearance is observed,
- the dynamic viscosity (μ) of each emulsion is measured at 20° C., by means of a Brookfield LVT type viscometer at a speed of 6 revolutions per minute (V6) when said dynamic viscosity is less than equal to approximately 100,000 mPa·s, equipped with a suitable mobile assembly or by means of a Brookfield RVT type viscometer at a speed of 5 revolutions per minute when said dynamic viscosity is greater than 100,000 mPa·s, equipped with a suitable mobile assembly.

The conductivity at 20° C. is measured by means of an LF 196 conductimeter by the company WTW equipped with a Tetracon™ 96 electrode.

The oil-in-water emulsions are then replaced and stored in the same insulated climatic chamber regulated at a temperature of 20° C. for up to three months. After a period of months, each emulsion is removed from the climatic chamber to observe the appearance thereof. The results obtained for the oil-in-water emulsions (E1) to (E13) according to the invention are recorded in table 3 below and the results obtained for the comparative oil-in-water emulsions ($F_1$) to ($F_{10}$) are recorded in table 4 hereinafter.

TABLE 3

| Emulsion | ($E_1$) | ($E_2$) | ($E_3$) | ($E_4$) | ($E_5$) | ($E_6$) | $E_7$) |
|---|---|---|---|---|---|---|---|
| Visual appearance after 7 days at 20° C. | ++ | ++ | ++ | ++ | ++ | ++ | ++ |
| Viscosity (Brookfield LVT, V6) in mPas. | 83,000 | 75,000 | 78,000 | 71,000 | 82,000 | 86,000 | 62,500 |
| Conductivity in mS · cm$^{-1}$ | 32.6 | 54.8 | 76.6 | 96.5 | 116.5 | 31.8 | 55.0 |
| Visual appearance after 3 months at 20° C. | ++ | ++ | ++ | ++ | ++ | ++ | ++ |

| Emulsion | ($E_8$) | ($E_9$) | ($E_{10}$) | ($E_{11}$) | ($E_{12}$) | ($E_{13}$) |
|---|---|---|---|---|---|---|
| Visual appearance after 7 days at 20° C. | ++ | ++ | ++ | ++ | ++ | ++ |
| Viscosity (Brookfield LVT, V6) in mPas. | 68,000 | 95,000 | 124,000* | 54,000 | 84,000 | 90,000 |
| Conductivity in mS · cm$^{-1}$ | 113.9 | 55.1 | 113.4 | 56.5 | 32.3 | 120.4 |
| Visual appearance after 3 months at 20° C. | ++ | ++ | ++ | ++ | ++ | ++ |

++: Homogeneous and smooth appearance
*dynamic viscosity measured at 20° C. with the Brookfield RVT viscometer, speed 5 revolutions per minute

TABLE 4

| | Emulsion | | | | |
|---|---|---|---|---|---|
| | ($F_1$) | ($F_2$) | ($F_3$) | ($F_4$) | ($F_5$) |
| Visual appearance after 7 days at 20° C. | (−) | (−) | (−) | (−) | (−) |
| Viscosity (Brookfield LVT, V6) in mPas. | 175,000* | 72,500 | 55,000 | 47,000 | 133,000* |
| Conductivity in mS · cm$^{-1}$ | 1.4 | 31.6 | 57.0 | 55.4 | 1.7 |
| Visual appearance after 3 months at 20° C. | (−−) | (−−) | (−−) | (−−) | (−−) |

| | Emulsion | | | | |
|---|---|---|---|---|---|
| | (F6) | (F7) | (F8) | (F9) | (F10) |
| Visual appearance after 7 days at 20° C. | (−) | (−) | (−) | (−) | (−) |
| Viscosity (Brookfield LVT, V6) in mPas. | 142,000* | 33,000 | 41,000 | 31,000 | 40,000 |
| Conductivity in mS · cm$^{-1}$ | 0.7 | 31.4 | 120.7 | 31.5 | 120.6 |
| Visual appearance after 3 months at 20° C. | (−−) | (−−) | (−−) | (−−) | (−−) |

*dynamic viscosity measured at 20° C. with the Brookfield RVT viscometer, speed 5 revolutions per minute.
(−): Presence of lumps and clusters
(−−): Heterogeneous appearance with presence of lumps and clusters 2-4: Analysis of the Results The results are deemed to be satisfactory when the visual appearance of an oil-in-water emulsion is deemed to be homogenous and smooth after a storage period of three months at 20° C. of said oil-in-water emulsion, and when the dynamic viscosity thereof measured at 20° C., by means of a Brookfield LVT type viscometer at a speed of 6 revolutions per minute, equipped with the suitable mobile assembly, is greater than or equal to 30,000 mPa·s.

The emulsions ($E_1$) to ($E_{13}$) according to the invention have a smooth appearance, devoid of lumps and clusters, even following a prolonged storage period of 3 months at 20° C.

On the other hand, the results obtained with the emulsions ($F_2$) and ($F_3$) show that, when the stabilising system of the oil-in-water emulsion consists solely of the polyelectrolyte ($PA_1$) in the presence of a quantity of 2% and 4% of sodium chloride, oil-in-water emulsions having a homogeneous and smooth appearance after a storage period of 7 days at 20° C. are not obtained.

In addition, the results obtained with the emulsion ($F_4$) show that when the stabilising system of the oil-in-water emulsions solely consists of Tara gum in the presence of 4% NaCl, oil-in-water emulsions having a homogeneous and smooth appearance after a storage period of 7 days at 20° C. are not obtained.

For "tara gum" to polyelectrolyte ($PA_1$) ratios by weight respectively equal to 1/1, 3/5 and 3/1 and in the absence of sodium chloride, the results obtained with the emulsions ($F_1$), ($F_5$) and ($F_8$) show that oil-in-water emulsions having a homogeneous and smooth appearance after a storage period of 7 days at 20° C. are not obtained.

The results obtained with the emulsions ($F_7$) and ($F_8$), ($F_9$) and ($F_{10}$) comprising respectively 2% by weight and 4% by weight of sodium chloride show that when the stabilising system consists of Tara gum and one of the polyelectrolytes ($PA_3$) or ($PA_4$), oil-in-water emulsions having a homogeneous and smooth appearance after a storage period of 7 days at 20° C. are not obtained.

The comparison of the results obtained with the oil-in-water emulsions ($E_1$) to ($E_{13}$) according to the invention with those obtained with the oil-in-water emulsions ($F_1$) to ($F_6$) according to the prior art, allow an improvement in the appearance of the salt-enriched oil-in-water emulsions to be shown, while retaining a high degree of viscosity, representing an additional technical effect induced by the invention according to the present patent application.

3-1: Preparation of Oil-in-Water Emulsions According to the Prior Art

Two oil-in-water emulsions, referenced ($F_{11}$) to ($F_{12}$), of which the proportions by weight of the constituents thereof are recorded in table 5 below, are prepared using the following method:

in a first beaker, at a temperature of 20° C., the polyelectrolyte $PA_1$ and Xanthan gum are dispersed progressively and successively in an oil phase under mechanical stirring at 80 revolutions per minute;

in a second beaker, at a temperature of 20° C., the aqueous phase comprising the water and the quantity by weight of salt required is prepared;

the content of the first beaker is progressively poured into the second beaker at a temperature of 20° C., under mechanical stirring using a deflocculator at 1200 revolutions per minute;

the mixture obtained is maintained under stirring for 10 minutes, then drained to obtain the oil-in-water emulsions ($F_{11}$) to ($F_{12}$).

TABLE 5

| | Emulsion | |
|---|---|---|
| | ($F_{11}$) | ($F_{12}$) |
| Oil phase: | | |
| C8-C10 Triglycerides | 15% | 15% |
| Stabilising system: | | |
| Polyelectrolyte ($PA_1$) | 1% | 1% |
| Keltrol™ CG-T[3] | 1% | 1% |
| Aqueous phase: | | |
| Water | Qs 100% | Qs 100% |
| Sodium chloride | 2% | 10% |
| Geogard™ 221 | 0.6% | 0.6% |

[3]Keltrol™ CG-T is xanthan gum marketed by the company CP Kelco

3-2: Preparation of Oil-in-Water Emulsions of the Remodelling "Rinse-Off" Cream Mask Type for Stressed and Weakened Hair According to the Invention and According to the Prior Art One oil-in-water emulsion according to the prior art referenced ($F_{13}$) and one oil-in-water emulsion according to the invention referenced ($E_{14}$), of which the proportions by weight of the constituents thereof are recorded in table 1 below, are prepared using the following method:

in a first beaker, an oil phase is prepared by successively introducing Lanol™ P, Lanol™ 99, jojoba oil and Montanov™ 82 at a temperature of 80° C., and then the polyelectrolyte $PA_1$ is successively dispersed, then Tara gum or xanthan gum under mechanical stirring at 80 revolutions per minute;

in a second beaker, at a temperature of 20° C., the aqueous phase comprising water, whereon butylene glycol, N-cocoyl amino acids, PECOSIL™ SPP 50, AMONYL™ DM, SEPICIDE™ HB and SEPICIDE™ CI are poured progressively and successively, is prepared;

the content of the first beaker is progressively poured into the second beaker at a temperature of 20° C., under mechanical stirring using a deflocculator at 1200 revolutions per minute;

the mixture obtained is maintained under stirring for 10 minutes, then drained to obtain the oil-in-water emulsions ($F_{13}$) and ($E_{14}$).

TABLE 6

| | Emulsion | |
|---|---|---|
| | ($F_{13}$) | ($E_{14}$) |
| Oil phase: | | |
| Jojoba oil | 1% | 1% |
| Lanol™P[4] | 6% | 6% |
| Lanol™99[5] | 5% | 5% |
| Montanov™82[6] | 3% | 3% |
| Stabilising system: | | |
| Polyelectrolyte (PA1) | 1% | 1% |
| Keltrol™ CG-T[3] | 1% | 0% |
| Tara gum[2] | 0% | 1% |
| Aqueous phase: | | |
| Water | Qs. 100% | Qs. 100% |
| Butylene Glycol | 3% | 3% |
| N-cocoyl amino acids | 0.7% | 0.7% |
| PECOSIL™SPP 50[7] | 0.75% | 0.75% |
| AMONYL™DM[8] | 1% | 1% |
| SEPICIDE™HB[9] | 0.3% | 0.3% |
| SEPICIDE™CI[12] | 0.2% | 0.2% |

[4]LANOL™ P is a glycol palmitate used as an additive with a stabilising effect, and marketed by the company SEPPIC.
[5]LANOL™ 99 is isononyl isononanoate marketed by the company SEPPIC.
[6]MONTANOV™ 82 is an emulsifying agent based on cetearyl alcohol and cocoylglucoside.
[7]PECOSIL™ SPP 50 is a potassium dimethicone PEG-7 panthenyl phosphate, marketed by the company PHOENIX.
[8]AMONYL™ DM is a cationic surfactant presented in the form of a quaternary ammonium salt, the INCI name of which is "Polyquaternium 82", and marketed by the company SEPPIC.
[9]SEPICIDE™ HB, which is a mixture of phenoxyethanol, methylparaben, ethylparaben and butylparaben, is a preservative marketed by the company SEPPIC.
(10): SEPICIDE™ CI, imidazoline urea, is a preservative marketed by the company SEPPIC.

3-3: Demonstration of the Properties and Characteristics of the Oil-in-Water Emulsions According to the Invention Compared to Oil-in-Water Emulsions According to the Prior Art The oil-in-water emulsions ($F_{11}$), ($F_{12}$) and ($F_{13}$) according to the prior art and the emulsion ($E_{14}$) according to the invention are evaluated according to the experimental protocol described in paragraph 2-3 above.

The results obtained with the oil-in-water emulsions ($F_{11}$), ($F_{12}$) and ($F_{13}$) according to the prior art and the results obtained with the emulsions ($E_{14}$) according to the invention are recorded in table 7 below.

TABLE 7

| | Emulsion | | | |
|---|---|---|---|---|
| | ($F_{11}$) | ($F_{12}$) | ($F_{13}$) | ($E_{14}$) |
| Visual appearance after 7 days at 20° C. | (−) | (−−) | (−) | (++) |
| Viscosity (Brookfield LVT, V6) in mPas. | 56,500 | 52,000 | 300,000* | 305,000* |
| Conductivity in mS · cm$^{-1}$ | 32.8 | 120.6 | 3.7 | 3.5 |
| Visual appearance after 3 months at 20° C. | (−−) | (−−) | (−−) | (++) |

(++): Homogeneous and smooth appearance
(−): Presence of lumps and clusters
(−−): Heterogeneous appearance with presence of lumps and clusters
*dynamic viscosity measured at 20° C. with the Brookfield RVT viscometer, speed 5 revolutions per minute.

3-4: Analysis of the Results

The results are deemed to be satisfactory when the visual appearance of an oil-in-water emulsion is deemed to be homogenous and smooth after a storage period of three months at 20° C. of said oil-in-water emulsion, and when the dynamic viscosity thereof measured at 20° C., by means of a Brookfield LVT type viscometer at a speed of 6 revolutions per minute, equipped with the suitable mobile assembly, is greater than or equal to 30,000 mPa·s.

The emulsions ($F_{11}$) and ($F_{12}$) according to the prior art should be compared respectively to the emulsions ($E_1$) and ($E_5$) according to the invention as they only differ in the compositions thereof by the use of xanthan gum instead of Tara gum in the stabilising system. The emulsions ($E_1$) and ($E_5$) have a smooth appearance, devoid of lumps and clusters, following a prolonged storage period of 3 months at 20° C., whereas the emulsions ($F_{11}$) and ($F_{12}$) exhibit a heterogeneous appearance with the presence of lumps and clusters after the same storage period under the same operating conditions.

Similarly, the oil-in-water emulsion ($E_{14}$) according to the invention has a smooth appearance, devoid of lumps and clusters, following a prolonged storage period of 3 months at 20° C., whereas the emulsion ($F_{13}$) according to the prior art exhibits a heterogeneous appearance with the presence of lumps and clusters after the same storage period under the same operating conditions.

The comparison of the results obtained with the oil-in-water emulsions ($E_1$), ($E_5$) and ($E_{14}$) according to the invention with those obtained with the oil-in-water emulsions ($F_{11}$), ($F_{12}$) and ($F_{13}$) according to the prior art, also enable an improvement in the appearance of the salt-enriched oil-in-water emulsions to be demonstrated, while retaining a high degree of viscosity, representing an additional technical effect induced by the invention according to the present patent application.

Example of Illustrative Formulas

4-1: Body Moisturising Treatment Cream Gel

Formula:

| A | Jojoba oil | 14.10% |
|---|---|---|
| | C12-C15 Alkyl Benzoate | 6.7% |
| | DC 25 | 4.2% |
| | DL alpha Tocopherol | 0.05% |
| B | Maris Aqua | 70.85% |
| | AQUAXYL™ | 3% |
| C | Polyelectrolyte ($PA_1$) | 2% |
| | Tara gum$^{(2)}$ | 1% |
| D | Euxyl™ PE9010 | 1% |
| | Fragrance | 0.1% |

Operating Method:

Mix the constituents of the oil phase A at a temperature of 80° C. under stirring. Then successively add the ingredients of phase C.

Prepare the aqueous phase B and heat it to 80° C. under stirring.

Add the aqueous phase B progressively to the mixture of phases A+C and emulsify by means of a stirrer equipped with a Silverson rotor-stator mobile assembly.

Then cool to 25° C., then add phase D.

Appearance after 1 day at 20° C.: homogeneous compact cream.

Dynamic viscosity after 1 day at 20° C.: 117,000 mPa·s (Brookfield RVT, M7, V5)

Appearance after 7 days at 20° C.: homogeneous compact cream.

Dynamic viscosity after 7 days at 20° C.: 105,000 mPa·s (Brookfield RVT, M7, V5)

Appearance after 1 month at 20° C.: homogeneous compact cream.

Dynamic viscosity after 1 month at 20° C.: 110,000 mPa·s (Brookfield RVT, M7, V5).

4-2: Face Mask Cream Gel

Formula:

| A | Triglycerides 4555 (C8C10) | 9% |
|---|---|---|
| | C12-C15 Alkyl Benzoate | 4% |
| | Isohexadecane | 2% |
| | DL alpha Tocopherol | 0.10% |
| B | Maris Aqua | qsp 100% |
| C | Polyelectrolyte ($PA_1$) | 1.3% |
| | Tara gum$^{(2)}$ | 0.7% |
| D | Euxyl PE9010 | 1% |
| | Fragrance | 0.1% |

Operating Method:

Mix the constituents of the oil phase A at a temperature of 80° C. under stirring. Then successively add the ingredients of phase C.

Prepare aqueous phase B and heat it to 80° C. under stirring.

Add aqueous phase B progressively to the mixture of phases A+C then emulsify by means of a stirrer equipped with a Silverson rotor-stator mobile assembly.

Then cool to 25° C. and add phase D.

Appearance after 1 day at 20° C.: Homogeneous compact cream.

Dynamic viscosity after 1 day at 20° C.: 71,000 mPa·s (Brookfield LVT, M4 V6)

Appearance after 7 days at 20° C.: Homogeneous compact cream.
Dynamic viscosity after 7 days at 20° C.: 78,400 mPa·s (Brookfield LVT, M4 V6)
Appearance after 1 month at 20° C.: Homogeneous compact cream.
Dynamic viscosity after 1 month at 20° C.: 79,100 mPa·s (Brookfield LVT, M4 V6).

4-3: Body Cream

Formula:

| | | |
|---|---|---|
| Triglycerides 4555 (C8C10) | 12% | |
| C12-C15 Alkyl Benzoate | 5.3% | |
| Isohexadecane | 2.7% | |
| Cetyl alcohol | 2% | |
| DL alpha Tocopherol | 0.10% | |
| Polyelectrolyte (PA$_1$) | 1.5% | |
| Tara gum$^{(2)}$ | 0.5% | |
| Water | qsp 100% | |
| Givobio™ GZn | 1% | |
| Sepicalm™ S | 3% | |
| Euxyl™ PE9010 | 1% | |
| Fragrance | 0.1% | |

4-4: Organomineral Sun Spray

Formula:

| | | |
|---|---|---|
| A | Isodecyl neopentanoate | 20% |
| | Cyclodimethicone | 5% |
| | Ethylhexylmethoxicinnamate | 6% |
| | Butyl Methoxydibenzoylmethane | 3% |
| | DL alpha Tocopherol | 0.05% |
| B | Water | Qs. 100% |
| | Tetrasodium EDTA | 0.2% |
| | Glycerin | 7% |
| | Phenyl benzimidazole sulfonic acid (salified with necessary molar quantity of soda) | 3% |
| C | Polyelectrolyte (PA$_1$) | 1.3% |
| | Tara gum$^{(2)}$ | 0.7% |
| D | SEPICIDE™ HB | 1% |
| | Fragrance | 0.1% |

AQUAXYL™ (INCI name: Xylitylglucoside & Anhydroxylitol & Xylitol): Moisturising composition marketed by the company SEPPIC.
Euxyl™ PE9010 (INCI name: Phenoxyethanol & Ethylhexyl Glycerin): composition used as preservative.
GIVOBIO™ GZn (INCI name: Zinc Gluconate): composition marketed by the company SEPPIC.
LANOL™ 99 (INCI name: Isononyl Isononanoate): ester used as oil phase in cosmetic composition preparation and distributed by the company SEPPIC.
Maris Aqua: sea water containing 8% sodium chloride.
SEPICIDE™ HB (INCI name: Phenoxyethanol/Methylparaben/Ethylparaben/Propylparaben/Butylparaben): preservative containing phenoxyethanol, marketed by the company SEPPIC.
SEPICALM™ S: (INCI name: Sodium Cocoyl Amino acids And Sarcosine And Potassium Aspartate And Magnesium Aspartate): anti-inflammatory composition marketed by the company SEPPIC.
SERENIKS™ 207 (INCI name: *Tsuga Canadensis* Leaf Extract And Water And Butylene Glycol) is an anti-aging composition.

The invention claimed is:

1. A composition (C$_1$) presented in the form of an oil-in-water type emulsion, comprising:
   from 5 to 55% by weight of an oil phase (P$_1$) comprising at least one oil and optionally at least one wax;
   from 0.025% to 3.75% by weight of at least one cross-linked anionic polyelectrolyte (PA), the PA resulting from polymerisation of
   partially or completely salified 2-methyl 2-[(1-oxo 2-propenyl) amino] 1-propane sulfonic acid with
   at least one neutral monomer selected from the group consisting of: acrylamide, (2-hydroxy ethyl) acrylate, N,N-dialkyl acrylamide, wherein each of the alkyl groups comprises between one and four carbon atoms, and at least one monomer of formula (I):

$$\text{(I)}$$

wherein R represents a linear or branched alkyl radical comprising from eight to twenty carbon atoms and n represents a number greater than or equal to one and less than or equal to twenty,
   in the presence of at least one cross-linking agent;
   from 0.025% to 3.75% by weight of at least one galactomannan (GM) having a degree of substitution (DS) of approximately 1/3; and
   from 37.5% to 94.95% by weight of a cosmetically acceptable aqueous phase (P$_2$), said aqueous phase (P$_2$) comprising from 1% to 25% by weight of at least one salt (S) presented in a dissolved form,
   wherein for said composition (C$_1$), the weight ratio between the at least one galactomannan (GM) and the cross-linked anionic polyelectrolyte (PA) is greater than or equal to 1/3 and less than or equal to 3/1.

2. The composition (C$_1$) of claim 1, wherein said cross-linked anionic polyelectrolyte (PA) comprises:
   from 20% molar to 80% molar of monomeric units from said partially or completely salified 2-methyl-2-[(1-oxo-2-propenyl) amino] 1-propane sulfonic acid;
   from 15% molar to 75% molar of monomeric units from said neutral monomer; and
   from 0.5% to 5% molar of monomeric units from said monomer of formula (I).

3. The composition (C$_1$) of claim 1, wherein said neutral monomer is acrylamide, (2-hydroxy ethyl) acrylate or N,N-dimethyl acrylamide.

4. The composition (C$_1$) of claim 1, wherein said monomer of formula (I) is tetraethoxylated lauryl methacrylate.

5. The composition (C$_1$) of claim 1, wherein said cross-linked anionic polyelectrolyte (PA) is a terpolymer of partially salified 2-methyl 2-[(1-oxo-2-propenyl) amino] 1-propane sulfonic acid in the form of ammonium salt, N,N-dimethyl acrylamide and tetraethoxylated lauryl methacrylate, cross-linked with trimethylol propanetriacrylate.

6. The composition (C$_1$) of claim 1, wherein said cross-linked anionic polyelectrolyte (PA) is a terpolymer of partially salified 2-methyl 2-[(1-oxo 2-propenyl) amino] 1-propane sulfonic acid in the form of ammonium salt, (2-hydroxy ethyl) acrylate and tetraethoxylated lauryl methacrylate, cross-linked with trimethylol propanetriacrylate.

7. The composition ($C_1$) of claim 1, wherein the salt (S) is an inorganic salt consisting of a cation that is an ammonium ion or a metal cation and of an anion selected from the elements of the group consisting of the halides, carbonates, bicarbonates, phosphates, nitrates, borates and sulfates.

8. The composition ($C_1$) of claim 1, wherein the salt (S) is an organic salt consisting of a cation that is an ammonium ion and of a metal cation and an organic anion that is an organic compound having at least one carboxylic acid function in carboxylate form or at least one sulfonic acid function in sulfonate form or at least one sulfate function.

9. The composition ($C_1$) of claim 1, wherein the salt (S) is an organic salt selected from the group consisting of sodium glycolate, sodium citrate, sodium salicylate, sodium lactate, sodium gluconate, zinc gluconate, manganese gluconate, copper gluconate and magnesium aspartate.

10. The composition ($C_1$) of claim 1, wherein the salt (S) is an organic salt selected from the group consisting of sodium 2-phenylbenzimidazole-5-sulfonate and sodium 4-hydroxy 2-methoxy 5-(oxo-phenylmethyl)benzene sulfonate.

11. The composition ($C_1$) of claim 1, wherein the dynamic viscosity thereof measured at a temperature of 20° C., by means of a Brookfield type viscometer, is greater than or equal to 30,000 mPa·s and less than or equal to 200,000 mPa·s.

12. A method for preparing the composition ($C_1$) of claim 1, comprising:
   at least one step a) for preparing a phase ($P'_1$) by mixing the cross-linked anionic polyelectrolyte (PA) and galactomannan (GM) in the oil phase ($P_1$); and
   at least one step b) for emulsifying said phase ($P'_1$) obtained following step a) with a cosmetically acceptable aqueous phase ($P_2$).

13. The composition ($C_1$) of claim 2, wherein said neutral monomer is chosen from acrylamide, (2-hydroxy ethyl) acrylate or N,N-dimethyl acrylamide.

14. The composition ($C_1$) of claim 2, wherein said monomer of formula (I) is tetraethoxylated lauryl methacrylate.

15. The composition ($C_1$) of claim 3, wherein said monomer of formula (I) is tetraethoxylated lauryl methacrylate.

16. The composition ($C_1$) of claim 2, wherein said cross-linked anionic polyelectrolyte (PA) is a terpolymer of partially salified 2-methyl 2-[(1-oxo 2-propenyl) amino] 1-propane sulfonic acid in the form of ammonium salt, N,N-dimethyl acrylamide and tetraethoxylated lauryl methacrylate, cross-linked with trimethylol propanetriacrylate.

17. The composition ($C_1$) of claim 3, wherein said cross-linked anionic polyelectrolyte (PA) is a terpolymer of partially salified 2-methyl 2-[(1-oxo 2-propenyl) amino] 1-propane sulfonic acid in the form of ammonium salt, N,N-dimethyl acrylamide and tetraethoxylated lauryl methacrylate, cross-linked with trimethylol propanetriacrylate.

18. The composition ($C_1$) of claim 4, wherein said cross-linked anionic polyelectrolyte (PA) is a terpolymer of partially salified 2-methyl 2-[(1-oxo 2-propenyl) amino] 1-propane sulfonic acid in the form of ammonium salt, N,N-dimethyl acrylamide and tetraethoxylated lauryl methacrylate, cross-linked with trimethylol propanetriacrylate.

19. The composition ($C_1$) of claim 2, wherein said cross-linked anionic polyelectrolyte (PA) is a terpolymer of partially salified 2-methyl 2-[(1-oxo 2-propenyl) amino] 1-propane sulfonic acid in the form of ammonium salt, (2-hydroxy ethyl) acrylate and tetraethoxylated lauryl methacrylate, cross-linked with trimethylol propanetriacrylate.

\* \* \* \* \*